(12) United States Patent
Compans et al.

(10) Patent No.: US 11,857,618 B2
(45) Date of Patent: Jan. 2, 2024

(54) BOOSTING IMMUNOGENICITY OF VACCINES USING SAPONINS AND AGONISTS OF THE INTRACELLULAR STIMULATOR OF INTERFERON GENES PATHWAY

(71) Applicant: Emory University, Atlanta, GA (US)

(72) Inventors: Richard Compans, Atlanta, GA (US); Elena Vassilieva, Roswell, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 17/233,333

(22) Filed: Apr. 16, 2021

(65) Prior Publication Data

US 2021/0322536 A1 Oct. 21, 2021

Related U.S. Application Data

(60) Provisional application No. 63/011,859, filed on Apr. 17, 2020.

(51) Int. Cl.
| | | |
|---|---|---|
| *A61K 39/145* | (2006.01) | |
| *A61K 39/39* | (2006.01) | |
| *A61P 31/16* | (2006.01) | |
| *A61K 39/00* | (2006.01) | |

(52) U.S. Cl.
CPC ............ *A61K 39/145* (2013.01); *A61K 39/39* (2013.01); *A61P 31/16* (2018.01); *A61K 2039/55* (2013.01); *A61K 2039/55555* (2013.01); *A61K 2039/55561* (2013.01); *A61K 2039/55577* (2013.01)

(58) Field of Classification Search
None
See application file for complete search history.

(56) References Cited

U.S. PATENT DOCUMENTS

| | | |
|---|---|---|
| 5,057,540 A | 10/1991 | Kensil |
| 6,231,859 B1 | 5/2001 | Kensil |
| 9,724,408 B2 | 8/2017 | Dubensky |
| 2007/0269379 A1 | 11/2007 | Mitragotri |
| 2018/0064745 A1 | 3/2018 | Katibah |
| 2018/0296663 A1* | 10/2018 | Hipp ............. A61K 39/00 |
| 2019/0125859 A1 | 5/2019 | Palese |

OTHER PUBLICATIONS

AddaVax (TM) Squalene-based oil-in-water adjuvant, Invivogen, 2020.
Burdette et al. STING is a direct innate immune sensor of cyclic-di-GMP, Nature, 478(7370): 515-518.
Calabro et al. The adjuvant effect of MF59 is due to the oil-in-water emulsion formulation,none of the individual components induce a comparable adjuvant effect, Vaccine, 2013, 31, 3363-3369.
Fernando et al. Potent Immunity to Low Doses of Influenza Vaccine by Probabilistic Guided Micro-Targeted Skin Delivery in a Mouse Model, PLoS ONE, 2010, 5(4): e10266.
Jacob et al. Membrane Cell Permeabilisation With Saponin and Multiparametric Analysis by Flow Cytometry, Cytometry, 12:550-558 (1991).
Jamur et al. Permeabilization of Cell Membranes, Chapter 9, Immunocytochemical Methods and Protocols, Methods in Molecular Biology, 2010 vol. 588, 63-66.
Langowski et al. Optimization of a Plasmodium falciparum circumsporozoite protein repeat vaccine using the tobacco mosaic virus platform, PNAS, 2020, 117 (6) 3114-3122.
Ng et al. Induction of potent CD8+ T cell responses through the delivery of subunit protein vaccines to skin antigen-presenting cells using densely packed microprojection arrays, Journal of Controlled Release 162 (2012) 477-484.
Ng et al. Potent response of QS-21 as a vaccine adjuvant in the skin when delivered with the Nanopatch, resulted in adjuvant dose sparing, Sci Rep, 2016, 6:29368.
Quil-A® Adjuvant Saponin vaccine adjuvant, InvivoGene, 2020.
RTS,S Clinical Trials Partnership, First Results of Phase 3 Trial of RTS,S/AS01 Malaria Vaccine in African Children, N Engl J Med, 2011, 365:1863-75.
Shingrix, Zoster Vaccine Recombinant, Adjuvanted, Vaccines and Related Biological Products Advisory Committee, 2017.
Skountzou et al., Skin immunization with influenza vaccines, Curr Top Microbiol Immunol, 2015, 386: 343-369.
STING, Deciphering the STING Paradox, Review InvivoGen, 2014.
Vassilieva et al. Combination of STING Pathway Agonist With Saponin Is an Effective Adjuvant in Immunosenescent Mice, Front. Immunol. 10:3006.
Junkins et al. A robust microparticle platform for a STING-targeted adjuvant that enhances both humoral and cellular Immunity during vaccination, J Control Release. 2018, 270: 1-13.

\* cited by examiner

*Primary Examiner* — Benjamin P Blumel
(74) *Attorney, Agent, or Firm* — Emory Patent Group

(57) ABSTRACT

This disclosure relates to boosting the immunogenicity of vaccines using an adjuvant combination comprising a saponin and an agonist of the intracellular stimulator of interferon genes pathway. In certain embodiments, the vaccine comprises an inactivated virus, attenuated virus, virus protein, virus like particle, or virosome. In certain embodiments, the human subject is of advanced age or elderly. In certain embodiments, the viral vaccine is an influenza vaccine.

1 Claim, 8 Drawing Sheets

BOOSTING IMMUNOGENICITY OF VACCINES USING SAPONINS AND AGONISTS OF THE INTRACELLULAR STIMULATOR OF INTERFERON GENES PATHWAY

CROSS-REFERENCE TO RELATED APPLICATIONS

This application claims the benefit of U.S. Provisional Application No. 63/011,859 filed Apr. 17, 2020. The entirety of this application is hereby incorporated by reference for all purposes.

STATEMENT REGARDING FEDERALLY SPONSORED RESEARCH OR DEVELOPMENT

This invention was made with government support under AI110680 awarded by the National Institutes of Health. The government has certain rights in the invention.

BACKGROUND

Viruses pose a substantial threat to human health. The use of live, attenuated viruses (LAVs) in vaccines elicit strong, protective immune responses. However, safety concerns for the elderly and immune suppressed have led to a shift toward the use of inactivated viruses or viral subunits as vaccines. Poor vaccine efficacy is prominent in elderly and immune suppressed populations. Influenza vaccination strategies for individuals over 65 years of age sometimes include administering a 4-fold higher dose of vaccine antigens per strain than is recommended for younger healthy adults. These approaches have not been universally successful. Thus, there is a need to identify improved vaccine strategies.

Kensil et al. report the use of saponins as immune adjuvants in vaccines. See U.S. Pat. Nos. 5,057,540, 6,231,859, and U.S. Published Application No. US2019/0125859.

Katbah et al. report cyclic dinucleotide immune stimulators that activate dendritic cells recognized as a pathogen associated molecular pattern, which bind to the pathogen recognition receptor known as Stimulator of INterferon Genes (STING). See U.S. Published Patent Application No. 2018/0064745.

Fernando et al. report immunity to low doses of influenza vaccine by probabilistic guided micro-targeted skin delivery in a mouse model. PLoS ONE, 2010, 5, e10266.

Ng et al. report the induction of CD8+ T cell responses through the delivery of subunit protein vaccines to skin antigen presenting cells using densely packed microprojection arrays. J Control Release, 2012, 162, 477-484.

References cited herein are not an admission of prior art.

SUMMARY

This disclosure relates to boosting the immunogenicity of vaccines using an adjuvant combination comprising a saponin and an agonist of the intracellular stimulator of interferon genes pathway. In certain embodiments, this disclosure relates to vaccination methods comprising administering, e.g., intramuscularly and/or intradermally, an effective amount of a vaccine in combination with a saponin and an agonist of the intracellular stimulator of interferon genes pathway to a subject such as a cyclic dinucleotide.

In certain embodiments, the subject is a human subject. In certain embodiments, the human subject is of advanced age, e.g., more than 45, 55, or elderly e.g., more than 65 years old. In certain embodiments, the viral vaccine is an influenza vaccine.

In certain embodiments, the saponin is a mixture of saponins purified from an aqueous extract of the bark of the South American tree, *Quillaia saponaria* Molina. In certain embodiments, the mixture of saponins comprises is Quil-A or purified *Quillaja saponins* QA-7, QA-17, QA-18, and QA-21. In certain embodiments, the mixture of saponins are formulated with squalene nanoparticles comprising sorbitan trioleate and polyoxyethylene sorbitan monooleate. In certain embodiments, the saponin is QA-21.

In certain embodiments, the agonist of the intracellular stimulator of interferon genes pathway is a cyclic dinucleotide or derivatives thereof. In certain embodiments, the cyclic dinucleotide is selected from a cyclic-di-AMP, cyclic-di-GMP, cyclic-di-IMP, cyclic-AMP-GMP, cyclic-AMP-IMP, cyclic-GMP-IMP, and cyclic-GMP-AMP (cGAMP). In certain embodiments, the cyclic dinucleotide has a fluoro substitution, e.g., for one or both 3'- or 2'-hydroxyls on cyclic-di-AMP, cyclic-di-GMP, cyclic-di-IMP, cyclic-AMP-GMP, cyclic-AMP-IMP, cyclic-GMP-IMP, or derivative thereof.

In certain embodiments, this disclosure relates to immunogenic compositions comprising vaccine compositions, a saponin, and an agonist of the intracellular stimulator of interferon genes pathway such as a cyclic dinucleotide. In certain embodiments, provided herein are devices, patches, and arrays of microneedles for use in intradermal administration wherein the devices, patches, or arrays are coated with vaccine compositions in combination with a saponin and an agonist of the intracellular stimulator of interferon genes pathway such as a cyclic dinucleotide. In certain embodiments, the vaccines comprise an inactivated virus, attenuated virus, virus protein, virus like particle, or virosome in combination with a saponin and an agonist of the intracellular stimulator of interferon genes pathway.

BRIEF DESCRIPTION OF THE SEVERAL VIEWS OF THE DRAWING(S)

FIG. 1A shows survival data.

Figure 1A:
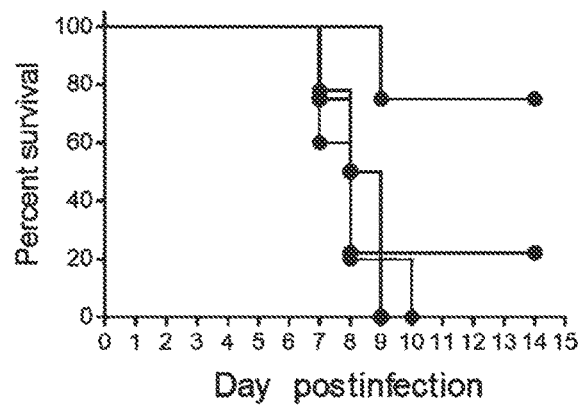
FIGS. 1A-1H show data on the effect of intradermal (ID) administration of 1 μg of A/California 07/09 (H1N1) vaccine supplemented with either 5 μg cGAMP or 5 μg Quil-A on protective immunity in aged mice.
Figure 1B:
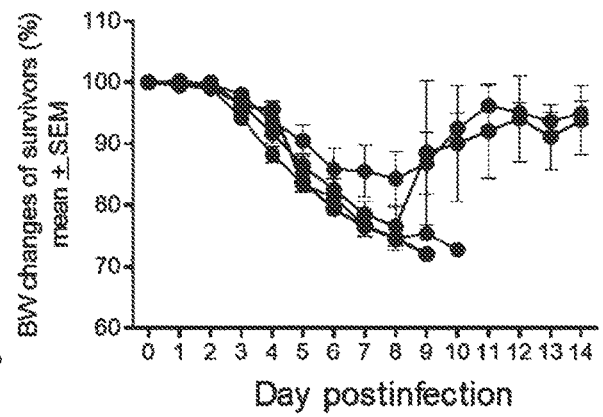
Figure 1C:
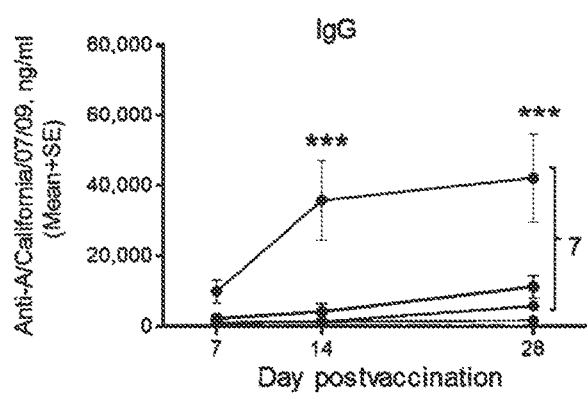

FIG. 1B a weight chart of the surviving mice challenged with mouse-adapted influenza A/California 07/09 H1N1 virus;

FIG. 1C shows data from a time course of vaccine-specific antibody IgG responses plotted against day post-vaccination. The data for days 14 and 28 are presented as means with the standard error of the mean, and inserts show individual data for each mouse at day 7 with boxes showing the 25-th and 75-th percentile. Delivery route observed at day 28 are indicated on each panel.

Figure 1D:
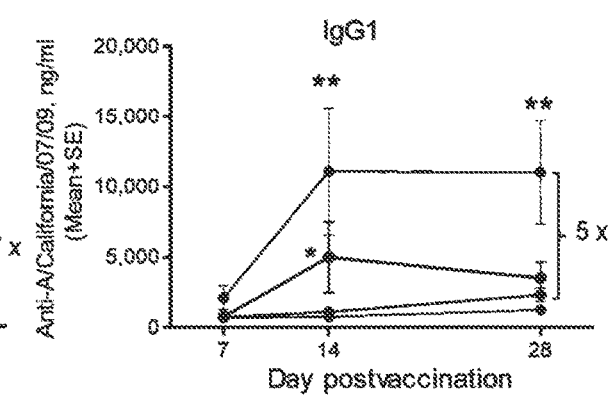

FIG. 1D shows data for IgG1.

Figure 1E:
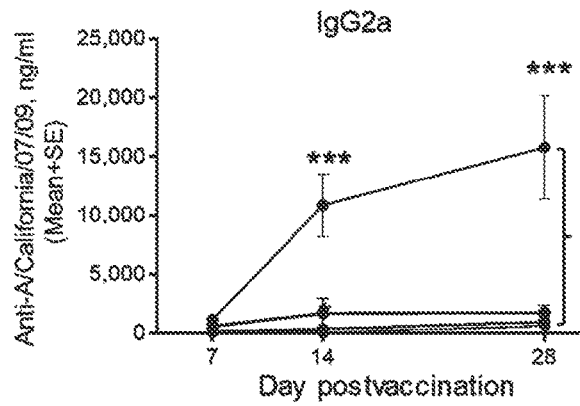

FIG. 1E shows data for IgG2a.

Figure 1F:
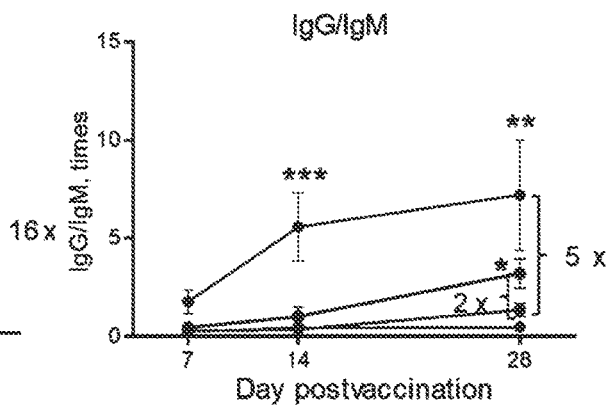

FIG. 1F shows data for the IgG:IgM ratio.

Figure 1G:
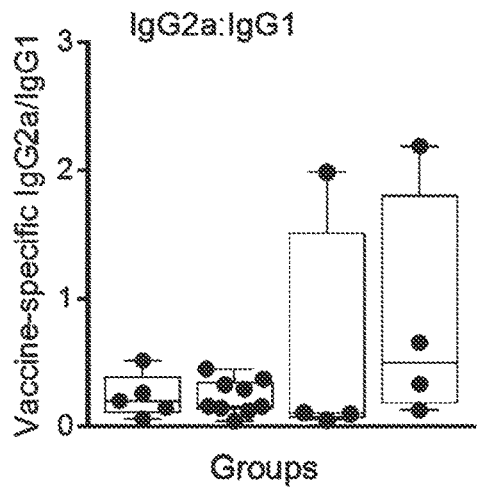

FIG. 1G shows data for vaccine-specific IgG2:IgG1 ratios measured at day 7 post-vaccination.

Figure 1H:
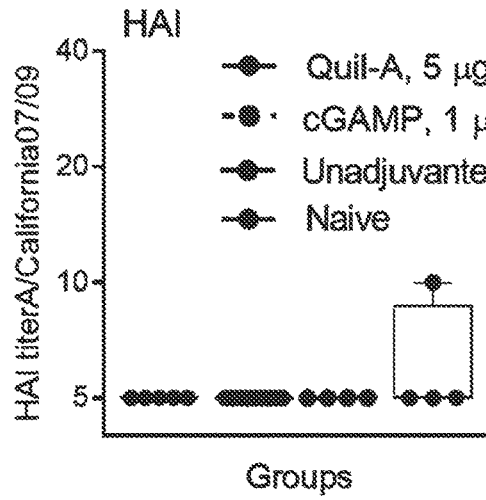

FIG. 1H shows data for HAI titers measured against A/California 07/09 H1N1 virus at day 28 post-vaccination. The titers below the detection level 10 were assigned a titer of 5 for calculations and converted to log 2 for statistical analysis.

FIGS. 2A-2H show data indicating a synergetic effect of cGAMP and Quil-A adjuvants co-delivered with 1 μg of A/California 07/09 (H1N1) vaccine in aged mice. Groups: light gray-naïve (n=5), solid lines and filled circles-vaccine only IM (n=4), broken lines and empty circles-vaccine only ID (n=9), black solid lines and filled circles—vaccine adjuvanted with 5 μg cGAMP+5 μg Quil-A IM (n=4), black broken lines and empty circles—vaccine adjuvanted with 5 μg cGAMP+5 μg Quil-A, ID (n=5).

Figure 2A:
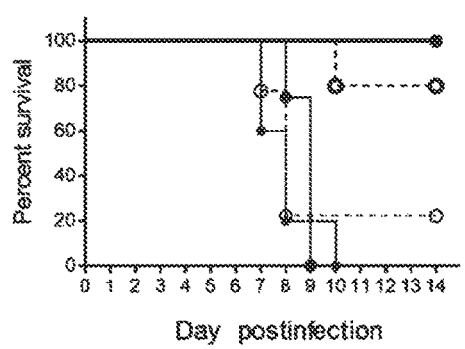

FIG. 2A shows survival data.

Figure 2B:
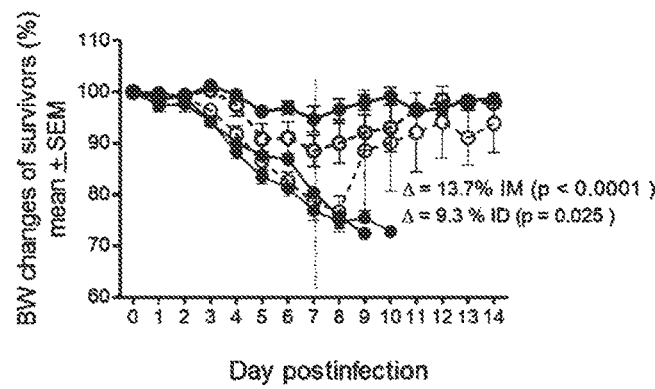

FIG. 2B shows a weight chart of the surviving mice challenged with mouse-adapted influenza A/California 07/09 H1N1 virus. Note significant differences in the average weight loss at day 7 post-challenge between unadjuvanted and adjuvanted groups delivered by the same route (ID or IM).

Figure 2C:
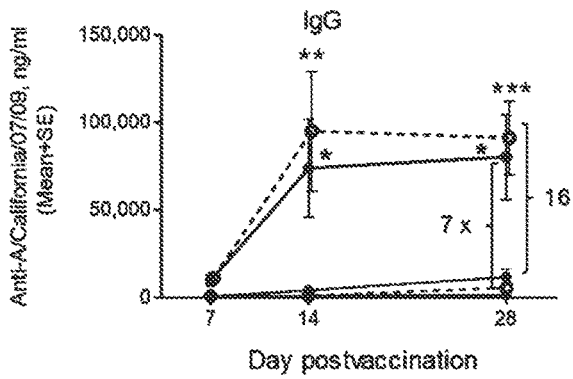

FIG. 2C shows a time course of vaccine-specific antibody IgG responses plotted against day post-vaccination.

Figure 2D:
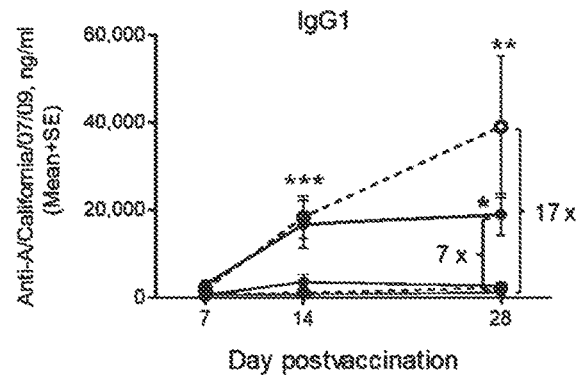

FIG. 2D shows data for IgG1.

Figure 2E:
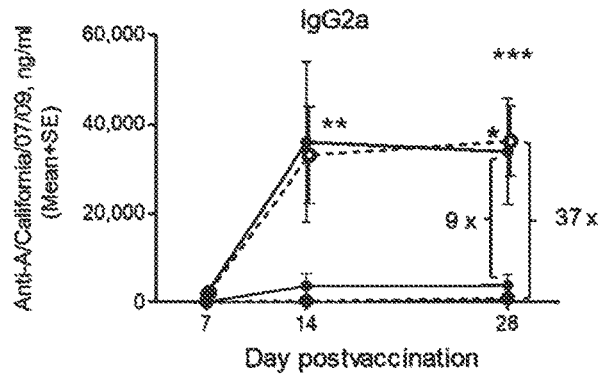

FIG. 2E shows data for IgG2a.

Figure 2F:
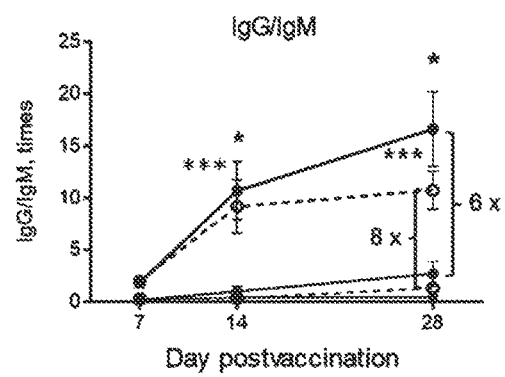

FIG. 2F shows data for the IgG:IgM ratios.

Figure 2G:
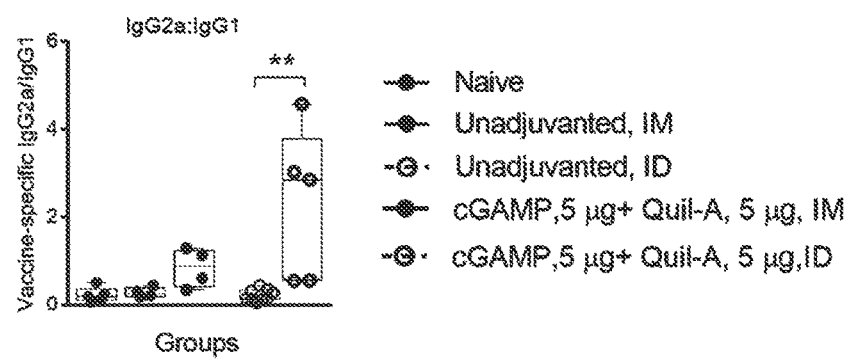

FIG. 2G shows data on vaccine-specific IgG2:IgG1 ratios measured at day 7 post-vaccination.

Figure 2H:
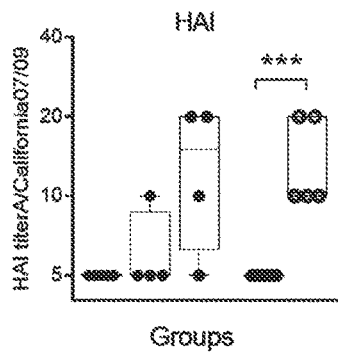

FIG. 2H shows data on HAI titers measured against A/California 07/09 H1N1 virus at day 28 post-vaccination.

Figure 3:
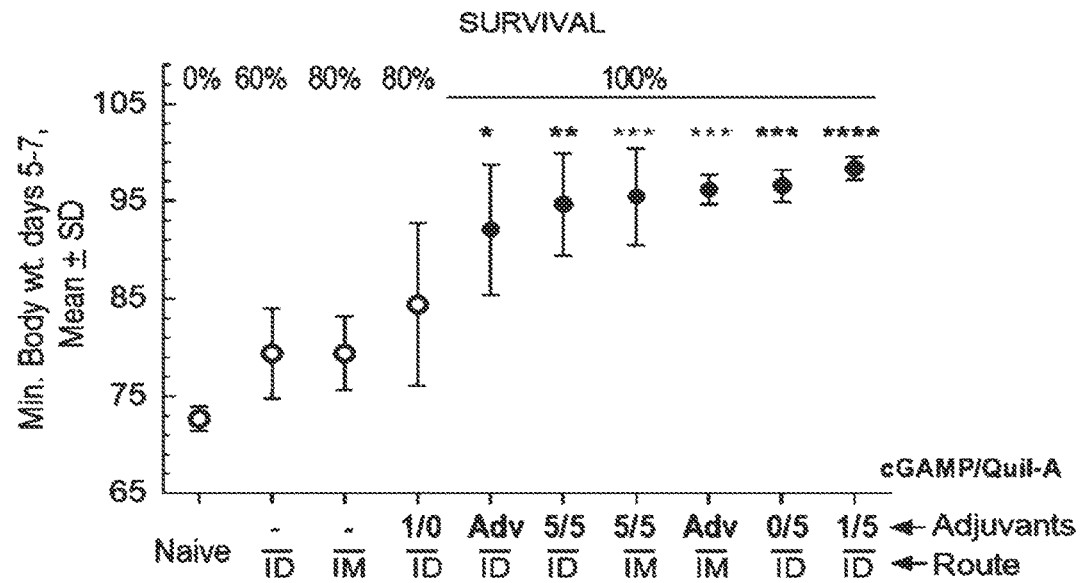

FIG. 3 shows data indicating protective efficacy of vaccination in adult mice, 5 per group except n=9 in the naïve group, vaccinated with 1 μg of A/California 07/09 (H1N1) vaccine and challenged with 70×$LD_{50}$ of mouse-adapted A/California 07/09 H1N1 virus. Average maximal weight loss relative to the pre-infection weight in each group between days 5-7 of challenge is plotted on the Y axis. Adjuvant composition and route of delivery for each group are indicated on the X axis; where a minus sign indicates unadjuvanted vaccine, AdV indicates AddaVax™ adjuvant, and numbers indicate the ratio of cGAMP to Quil-A, μg/μg. Empty circles represent groups with partial survival indicated by percentage on the top of the graph; filled circles represent groups with 100% survival. Light circles represent AddaVax™-adjuvanted groups. Black and gray stars indicate level of statistical significance between unadjuvanted and adjuvanted ID and IM groups, respectively.

FIGS. 4A-D show a comparison of the time course of antibody response between ID-vaccinated adult and aged mice. Groups: gray-naïve (n=5 in aged, 9 in adults); light-vaccine only (n=9 in aged, 5 in adults); dark-vaccine+5 μg Quil-A (n=4 in aged, 5 in adults); black-vaccine+5 μg Quil-A+5 μg cGAMP (n=5 in aged and in adults). Stars indicate significance levels of the differences between adjuvanted and non-adjuvanted group at the same time post-vaccination.

Figure 4A:
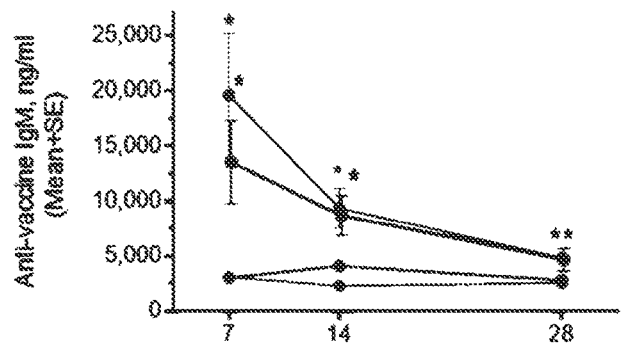

FIG. 4A shows data for vaccinated adult mice with vaccine-specific IgM. Y scale is linear.

Figure 4B:
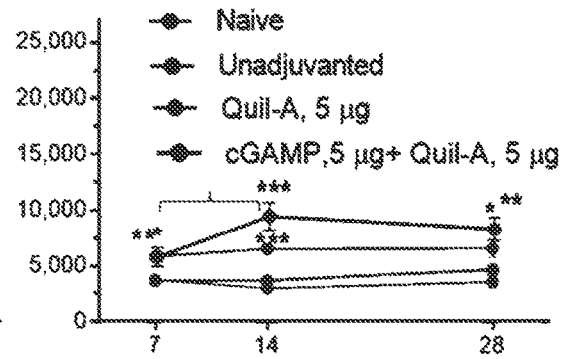

FIG. 4B shows data for vaccinated aged mice with vaccine-specific IgM. Y scale is linear. The bracket denotes a 1.6-fold increase (p=0.04) in vaccine-specific IgM level between days 7 and 14.

Figure 4C:
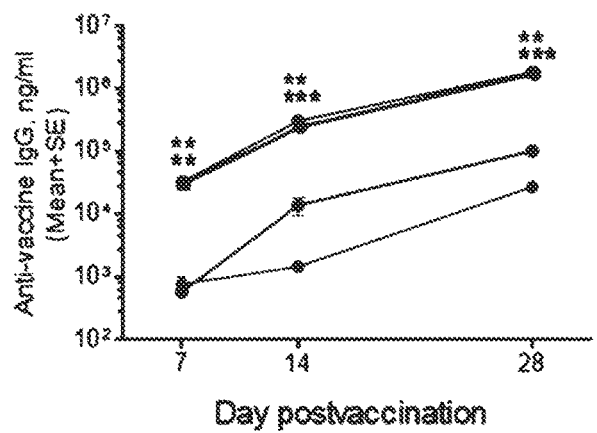

FIG. 4C shows data for vaccinated adult mice with vaccine-specific IgG. Y scale is logarithmic.

Figure 4D:
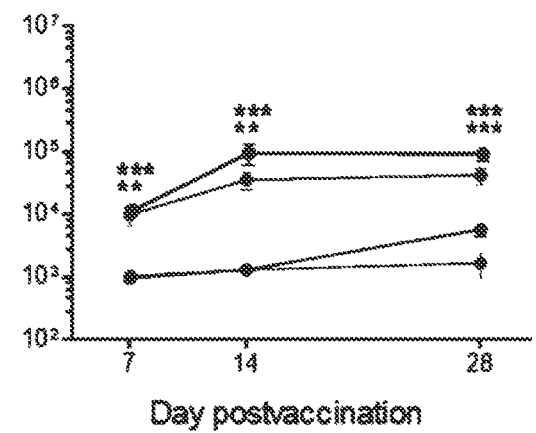

FIG. 4D shows data for vaccinated aged mice with vaccine-specific IgG. Y scale is logarithmic.

Figure 5A:
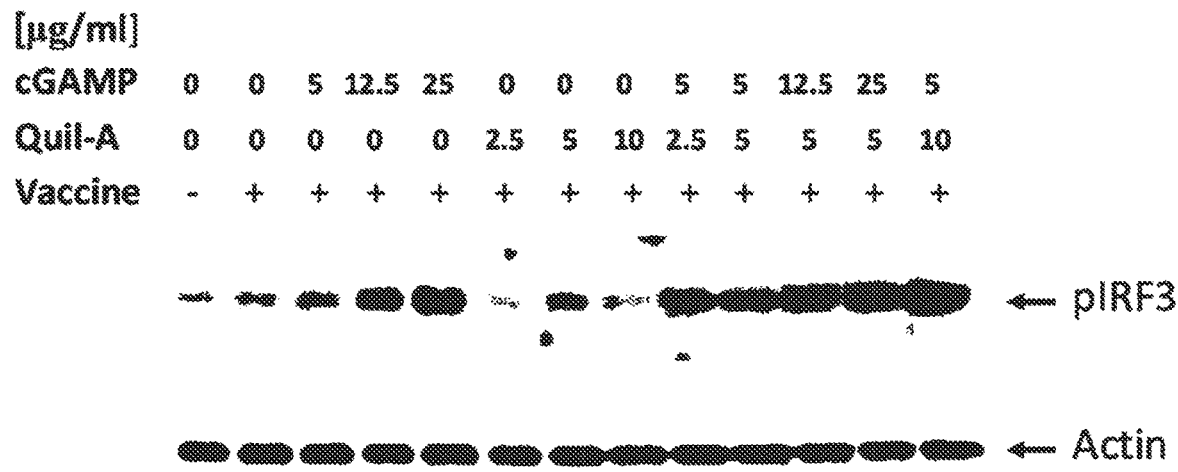
Figure 5B:
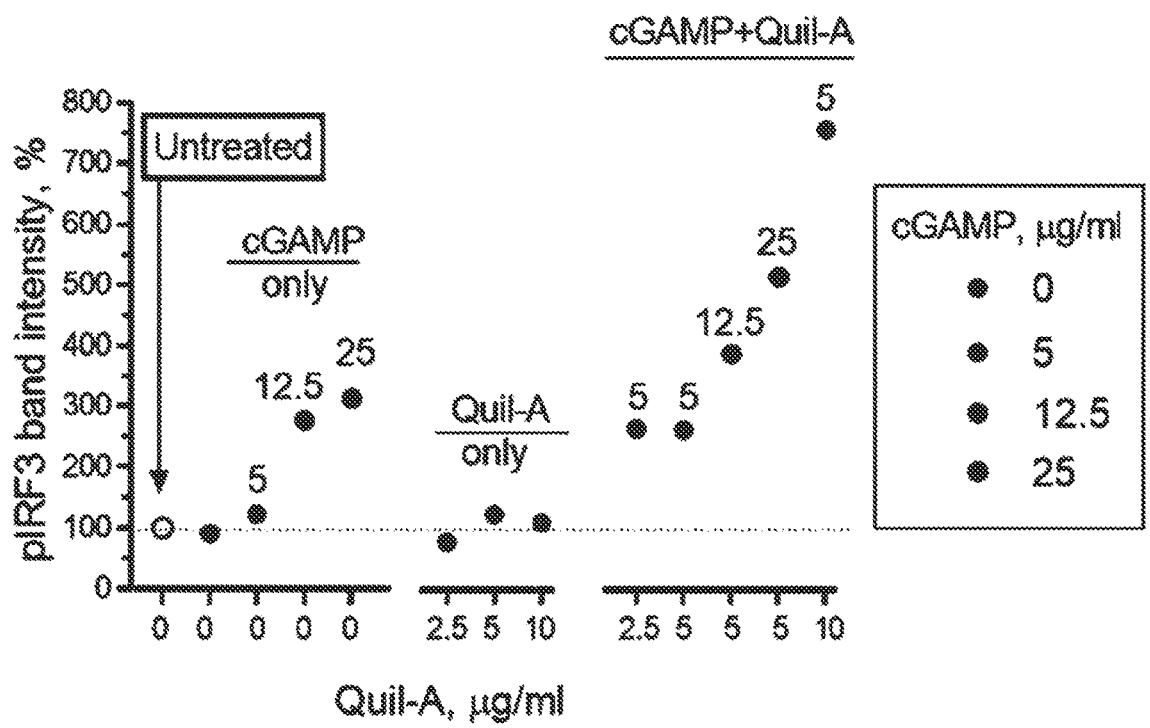

FIGS. 5A-B show data indicating phosphorylation of IRF3 in HeLa cells induced by Quil-A and cGAMP separately or in combination.

FIG. 5A is a representative western blot analysis of HeLa cell lysates prepared from cells treated for 1 h under conditions indicated for each lane. Concentration of vaccine was 5 μg/ml, concentrations of cGAMP and Quil-A varied from 0 to 25 μg/ml and from 0 to 10 μg/ml, respectively, as indicated for each condition.

FIG. 5B shows data on the intensity of the actin-normalized about 43 kDa pIRF3 band detected in the treated cell lysates relative to the non-treated cells (empty circle and dotted line correspond to first lane on the blot) is plotted against Quil-A concentration (X axis).

FIGS. 6A-H show data on the effect of AddaVax™ adjuvant co-administered with 1 μg of A/California 07/09 (H1N1) vaccine in aged mice. Groups: Gray-naïve (n=5), light solid lines and filled circles-unadjuvanted vaccine IM (n=4), broken lines and empty circles-unadjuvanted vaccine ID (n=9), black solid lines and filled circles-vaccine+AddaVax™ IM (n=5), dark broken lines and empty circles-vaccine+AddaVax™ ID.

Figure 6A:
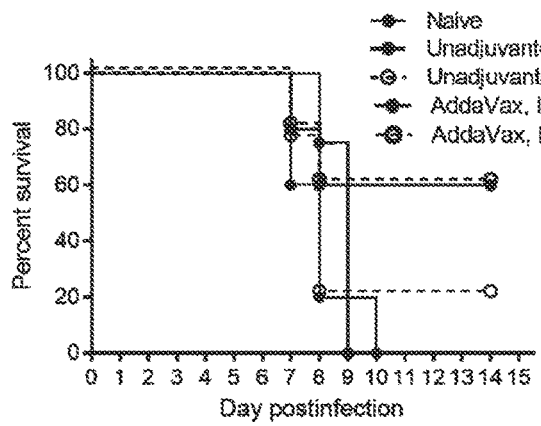

FIG. 6A shows survival data of the surviving mice challenged with mouse-adapted influenza A/California 07/09 H1N1 virus.

Figure 6B:
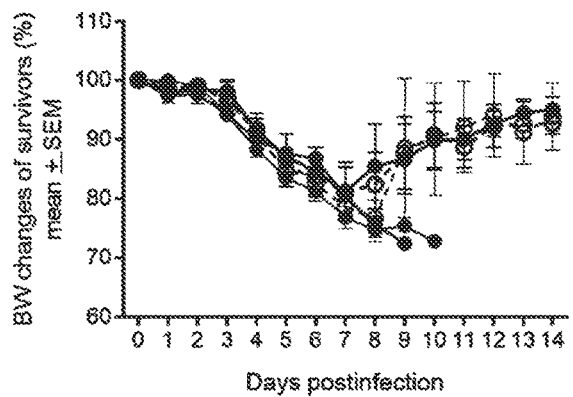

FIG. 6B shows weight data.

Figure 6C:
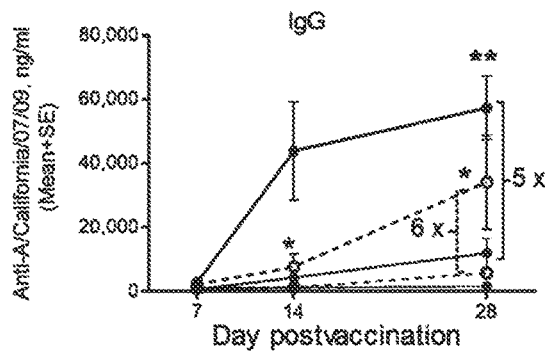

FIG. 6C shows time course of vaccine-specific IgG antibody response plotted against day post-vaccination.

Figure 6D:
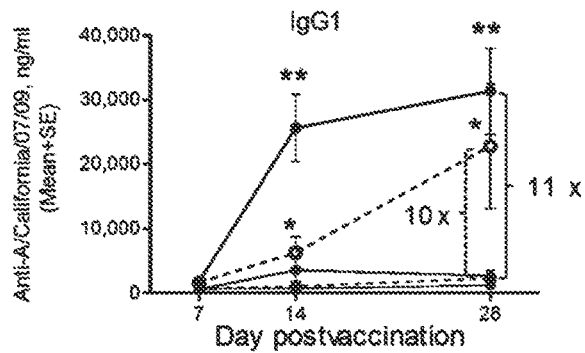

FIG. 6D shows data for IgG1.

Figure 6E:
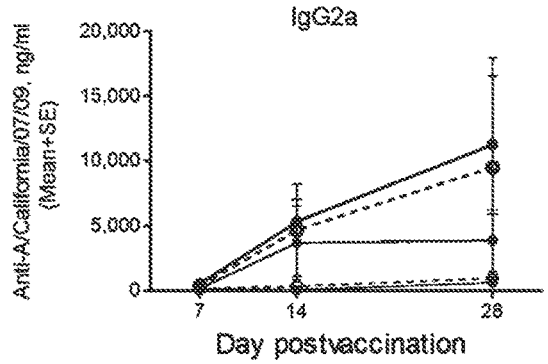

FIG. 6E shows data for IgG2a.

Figure 6F:
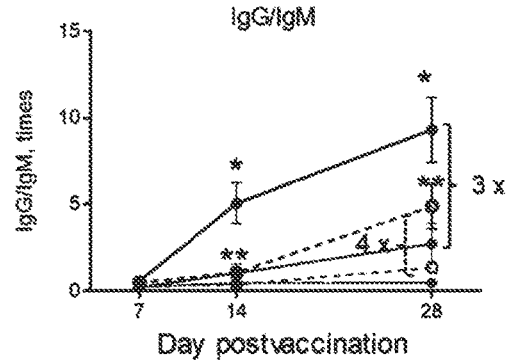

FIG. 6F shows data on the IgG:IgM ratios.

Figure 6G:
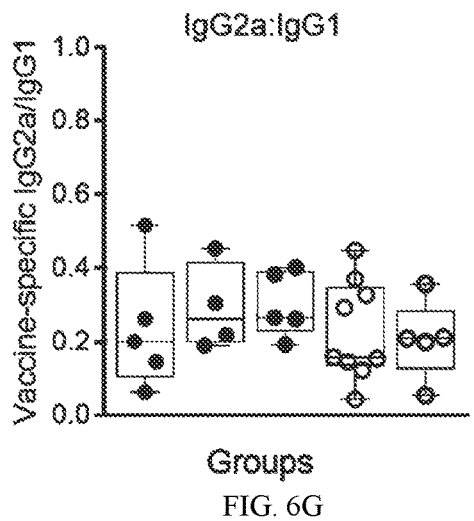

FIG. 6G shows data on vaccine-specific IgG2:IgG1 ratios measured at day 7 post-vaccination.

Figure 6H:
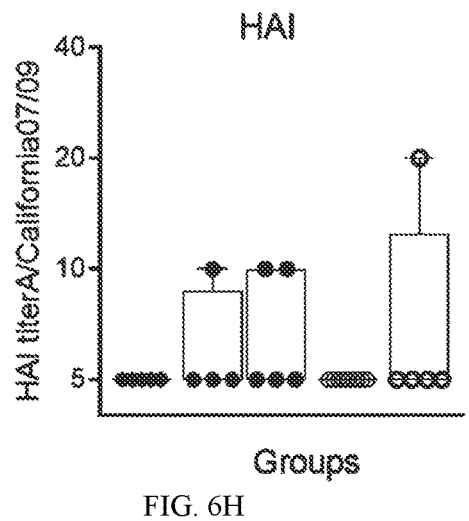

FIG. 6H shows data on HAI titers measured against A/California 07/09 H1N1 virus at day 28 post-vaccination.

FIGS. 7A-H show data on the effect of ID vaccination on protective immunity in aged mice using a 4-fold higher dose (4 μg) of vaccine antigen in comparison to the regular 1 μg dose. Groups: light gray—Naïve (n=5), grey-vaccine only (n=9), dark −4× vaccine (n=4).

Figure 7A:
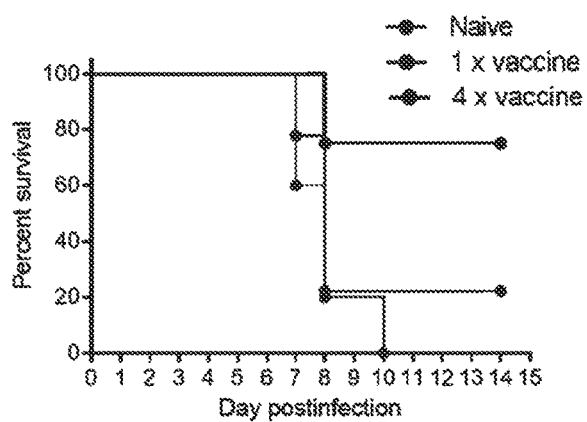

FIG. 7A shows survival data.

Figure 7B:
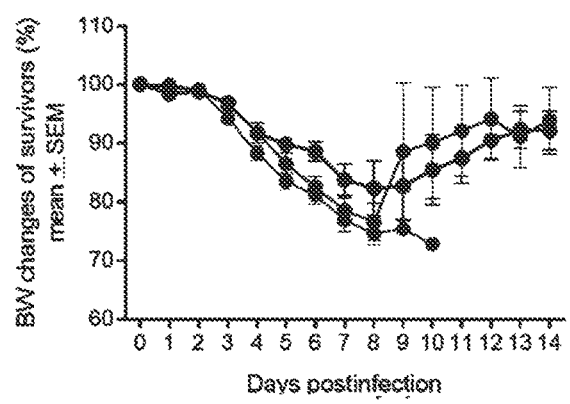

FIG. 7B shows a weight chart of the surviving mice challenged with the same virus.

Figure 7C:
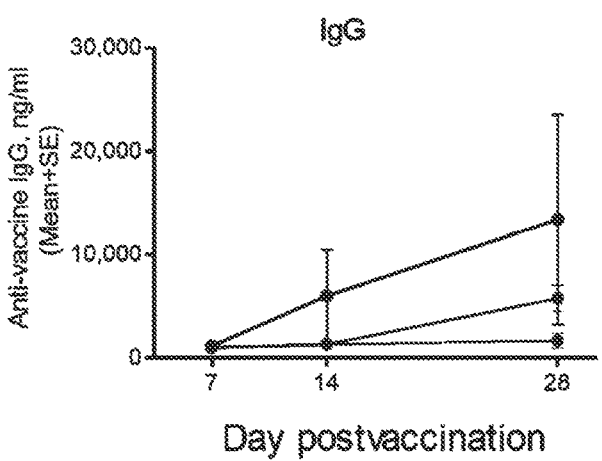

FIG. 7C shows data on time course of vaccine-specific IgG antibody responses plotted against day of vaccination.

Figure 7D:
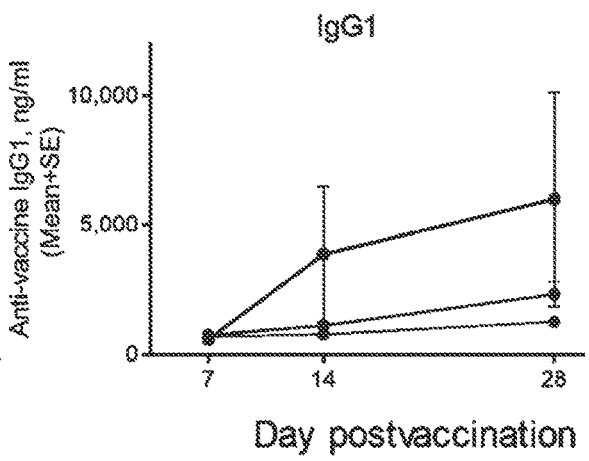

FIG. 7D shows data on IgG1.

Figure 7E:
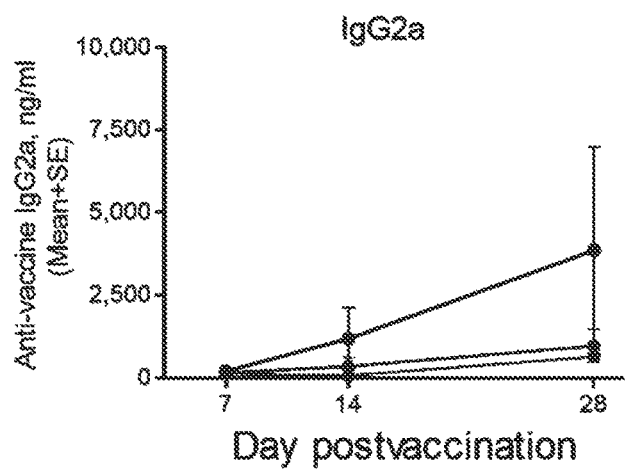

FIG. 7E shows data on IgG2a.

Figure 7F:
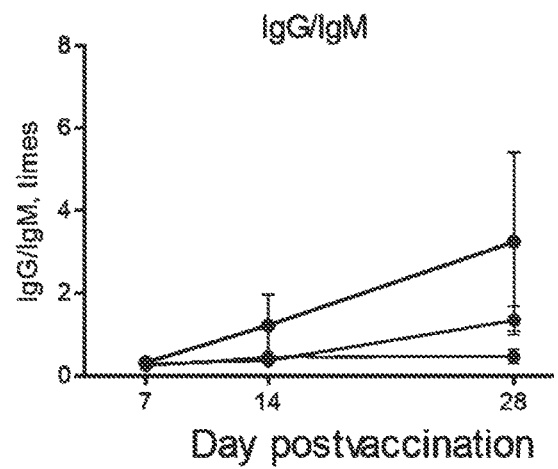

FIG. 7F shows data on the IgG:IgM ratio. The data for days 14 and 28 are presented as means with the standard error of mean, and inserts show individual data for each mouse at day 7 with the boxes showing the 25-th and 75-th percentile, the median, and whiskers between minimum, and maximum points. Statistically significant fold-differences between the means in unadjuvanted and adjuvanted groups vaccinated by the same delivery route observed for day 28 are indicated on each panel.

Figure 7G:
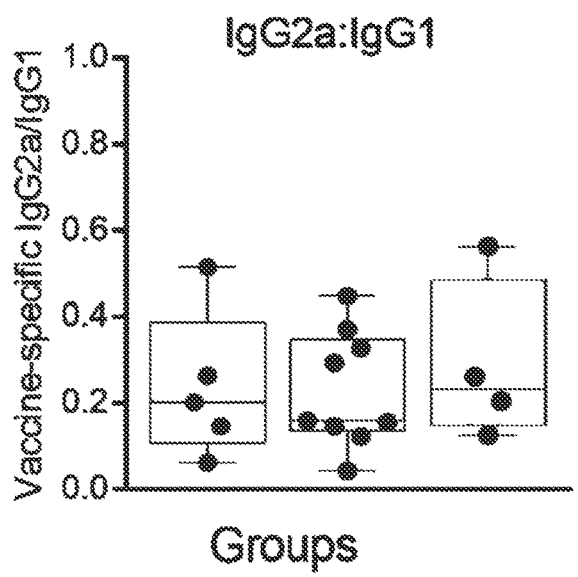

FIG. 7G shows data on vaccine-specific IgG2:IgG1 ratios at day 7 of vaccination.

Figure 7H:
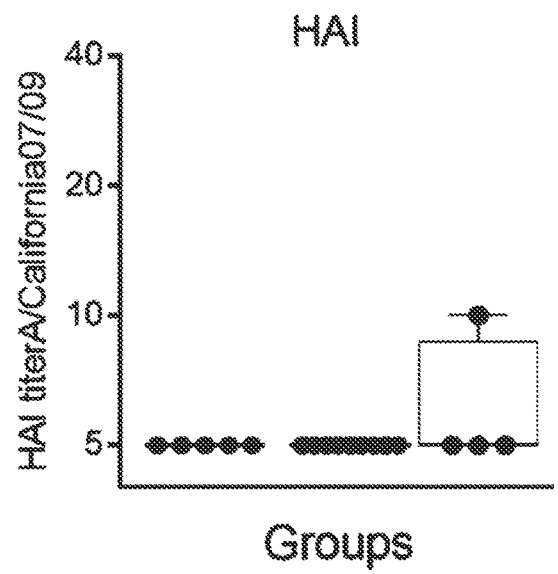

FIG. 7H shows data on HAI titers measured against A/California 07/09 H1N1 virus at day 28 of vaccination.

DETAILED DESCRIPTION OF THE INVENTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

"Subject" refers to any animal, preferably a human patient, livestock, rodent, monkey or domestic pet.

As used herein, the term "combination with" when used to describe administration with an additional treatment means that the agent may be administered prior to, together with, or after the additional treatment, or a combination thereof. As used herein, the term "intermixed with" when used to describe administration in combination with an additional treatment means that the agent may be administered "together with."

In certain embodiments, an "effective amount" in the context of administration of a therapy to a subject refers to the amount of a therapy which is sufficient to achieve one, two, three, four, or more of the following effects: (i) reduce or ameliorate the severity of a viral infection, disease or symptom associated therewith; (ii) reduce the duration of a viral infection, disease or symptom associated therewith; (iii) prevent the progression of a viral infection, disease or symptom associated therewith; (iv) cause regression of a viral infection, disease or symptom associated therewith; (v) prevent the development or onset of a viral infection, disease or symptom associated therewith; (vi) prevent the recurrence of a viral infection, disease or symptom associated therewith; (vii) reduce or prevent the spread of a viral from one cell to another cell, one tissue to another tissue, or one organ to another organ; (viii) prevent or reduce the spread of a viral from one subject to another subject; (ix) reduce organ failure associated with a viral infection; (x) reduce hospitalization of a subject; (xi) reduce hospitalization length; (xii) increase the survival of a subject with a viral infection or disease associated therewith; (xiii) eliminate a viral infection or disease associated therewith; (xiv) inhibit or reduce viral replication; (xv) inhibit or reduce the entry of an virus into a host cell(s); (xvi) inhibit or reduce replication of the virus genome; (xvii) inhibit or reduce synthesis of virus proteins; (xviii) inhibit or reduce assembly of virus particles; (xix) inhibit or reduce release of virus particles from a host cell(s); (xx) reduce virus titer; and/or (xxi) enhance or improve the prophylactic or therapeutic effect(s) of another therapy.

In certain embodiments, the effective amount does not result in complete protection from an influenza virus disease but results in a lower titer or reduced number of viruses compared to an untreated subject with a viral infection. In certain embodiments, the effective amount results in a 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of virus relative to an untreated subject with a viral infection. Benefits of a reduction in the titer, number or total burden of virus include, but are not limited to, less severe symptoms of the infection, fewer symptoms of the infection and a reduction in the length of the disease associated with the infection.

"HA" and "hemagglutinin" refer to any hemagglutinin known to those of skill in the art. In certain embodiments, the hemagglutinin is influenza hemagglutinin, such as an influenza A hemagglutinin, an influenza B hemagglutinin, or an influenza C hemagglutinin. A typical hemagglutinin comprises domains known to those of skill in the art including a signal peptide (optional herein), a stem domain, a globular head domain, a luminal domain (optional herein), a transmembrane domain (optional herein) and a cytoplasmic domain (optional herein).

"NA" and "neuraminidase" refer to any neuraminidase known to those of skill in the art. In certain embodiments, the neuraminidase is influenza neuraminidase, such as an influenza A neuraminidase, an influenza B neuraminidase, or an influenza C neuraminidase. As used herein, the terms "neuraminidase" and "NA" encompass neuraminidase polypeptides that are modified by post-translational processing such as disulfide bond formation, glycosylation (e.g., N-linked glycosylation), protease cleavage and lipid modification (e.g. S-palmitoylation).

As used herein, the terms "chimeric influenza virus hemagglutinin polypeptide," "chimeric influenza virus HA polypeptide," "chimeric hemagglutinin polypeptide," "chimeric HA," "chimeric hemagglutinin," and "chimeric influenza hemagglutinin polypeptide" refer to an influenza hemagglutinin that comprises an influenza virus hemagglutinin stem domain and an influenza virus hemagglutinin head domain, wherein the influenza virus hemagglutinin head domain is heterologous to the influenza virus hemagglutinin stem domain.

As used herein, the term "heterologous" in the context of a polypeptide, nucleic acid or virus refers to a polypeptide, nucleic acid or virus that is not normally found in nature or not normally associated in nature with a polypeptide, nucleic acid, or virus of interest. For example, a "heterologous polypeptide" may refer to a polypeptide derived from a different virus, e.g., a different influenza strain or subtype, or an unrelated virus or different species. In specific embodiments, when used in the context of a globular head domain of a chimeric influenza virus hemagglutinin described herein, the term heterologous refers to an influenza HA globular head domain that is associated with an influenza HA stem domain that it would not normally be found associated with (e.g., the head and stem domains of the HA would not be found together in nature).

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

Vaccines and Adjuvant Mixtures

Viral vaccines are typically produced by injection of a desired viral strain into eggs, or other cells, and incubation for several days to allow the viruses to replicate. The fluid containing virus is harvested. For inactivated vaccines, virus nucleic acids are completely inactivated (or killed) with a chemical, for example, formalin or beta-propiolactone, or by physical means. After, the virus antigens are typically purified prior to use in the vaccine.

Influenza viruses may be propagated in embryonated chicken eggs. The virus-containing fluids are harvested and inactivated with formaldehyde. Influenza virus may be concentrated and purified in a linear sucrose density gradient solution using a continuous flow centrifuge. The virus may be chemically disrupted using a nonionic surfactant, octoxinol-9, producing a "split virus." The split virus may be further purified by chemical means and suspended in sodium phosphate-buffered isotonic sodium chloride solution.

Attenuated vaccines are those created by passaging a virus in cultured cells. Virus strains are selectively and repeatedly exposed to, collected, and subsequently grown in non-human cells. Repeatedly selecting strains most capable of non-human cell infection and replication are eventually weakened in their ability to infect human cells, e.g., virus that are selected as superior at entering the chicken cells become less able to infect human cells.

Viruses may also be attenuated by deleterious gene mutation, altered replication fidelity, codon deoptimization. Recombinant viral vaccines also may be created synthetically using recombinant techniques. A DNA plasmid encoding a viral antigen may be combined with a baculovirus. The role of the baculovirus is to help transport the DNA instructions for making the viral antigen and/or proteins that assemble into a virus like particle containing the viral antigen but lack intact viral nucleic acids. Once the recombinant virus enters a host cell line, the cells produce the viral antigens or particles containing the same.

In certain embodiments, this disclosure relates to methods for inducing an immune response (e.g., an antibody response) against a virus, such as influenza virus, using a viral vaccine, e.g., an influenza viral vaccine, and an adjuvant mixture comprising a saponin and an agonist of the intracellular stimulator of interferon genes pathway such as cyclic dinucleotide.

In certain embodiments, immunization regimens involve the intradermal administration of an effective amount of a hemagglutinin, chimeric hemagglutinin, a headless hemagglutinin or another influenza virus stem domain based construct (e.g., the hemagglutinin stem domain or a fragment thereof) in combination with saponins and an agonist of the intracellular stimulator of interferon genes pathway to a subject. In certain aspects, the immunization regimens also involve the administration of an influenza virus hemagglutinin (HA) and/or neuraminidase (NA) immunogen(s). Also provided herein are vaccine compositions for use in methods of immunizing against influenza virus in human subjects. A full-length influenza hemagglutinin typically comprises an HA1 domain and an HA2 domain. In certain embodiments, a globular head domain is heterologous to the stem domain formed by the other segments of the HA1 domain and the HA2 domain.

In some embodiments, the immunization/vaccinating regimens involve intradermally administering to the subject an immunogenic composition comprising an inactivated influenza virus in combination with saponins and an agonist of the intracellular stimulator of interferon genes pathway to a subject. In certain embodiments, the inactivated influenza virus comprises a hemagglutinin (HA) or chimeric HA and optionally a neuraminidase (NA).

In certain embodiments, the chimeric HA comprises an influenza virus HA globular head domain and the HA stem domain, wherein the globular head domain is heterologous to the HA stem domain. In certain embodiments, the HA stem domain of the chimeric HAs are from one influenza virus subtype, and the HA globular head domains of the chimeric HAs are from other influenza virus subtypes. In certain embodiments, the HA stem domain of the chimeric HAs is from an influenza virus H1 or H3 subtype. In some embodiments, the influenza virus HA globular head domain is from an influenza A virus H4, H5, H7, H8, H11, H12, H14 or H15 subtype. In certain embodiments, the influenza virus HA globular head domain is the influenza virus HA globular head domain of an influenza virus of subtype H4, H6, H7, H9, H10, H11, H12, H13, H14, H15, H16, H17, or H18. In some embodiments, the influenza virus neuraminidase polypeptide is from an influenza virus of subtype N1, N2, N3, N4, N5, N6, N7, N8, N9, N10, and/or N11 In certain embodiments, provided herein is a method for immunizing against influenza virus in a human subject, comprising (a) administering to the subject a first vaccine comprising a chimeric HA, a headless HA or another influenza virus stem domain based construct (e.g., the HA stem domain or a fragment thereof), or an influenza virus hemagglutinin core polypeptide and/or an NA immunogen(s) or a vector comprising such a construct; and (b) a certain time after the administration of the first vaccine formulation, intradermally administering to the subject an inactivated influenza virus vaccine, or a vector comprising such a construct in combination with saponins and an agonist of the intracellular stimulator of interferon genes pathway.

In certain embodiments, the second immunogenic composition is administered about 6 weeks, about 12 weeks, about 4 months, about 6 months, or about 9 months after the administration of the first immunogenic composition. In another specific embodiment, the second immunogenic composition is administered 1 week to 9 months, 3 weeks to 8 months, 6 weeks to 12 weeks, 4 weeks to 6 months, 5 weeks to 5 months, 6 weeks to 4 months, 7 weeks to 4 months, 8 weeks to 4 months, 8 weeks to 3 months, 3 months to 6 months, 3 months to 9 months, or 6 months to 9 months after the administration of the first immunogenic composition.

Viral polypeptides described herein can be incorporated into virus-like particle (VLP) vectors, e.g., purified/isolated VLPs. VLPs generally comprise viral polypeptide(s) derived from a structural protein(s) of a virus. In some embodiments, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art.

In specific embodiments, VLPs, e.g., VLPs comprising an influenza hemagglutinin (HA) polypeptide and/or an influenza virus neuraminidase (NA) polypeptide, are expressed in cells (such as, e.g., mammalian cells (e.g., 293T cells) and insect cells (e.g., High Five cells and Sf9 cells). In certain embodiments, the VLPs are expressed in cells that express surface glycoproteins that comprise sialic acid. In accordance with such embodiments, the cells are cultured in the presence of neuraminidase. In certain embodiments, VLPs, e.g., VLPs comprising an influenza hemagglutinin (HA) polypeptide and/or an influenza virus neuraminidase polypeptide, are expressed in cells that do not express surface glycoproteins that comprise sialic acid.

In certain embodiments, a viral polypeptide may be incorporated into a virosome. A virosome containing a viral polypeptide and/or an influenza virus polypeptide may be produced using techniques known to those skilled in the art. For example, a virosome may be produced by disrupting a purified virus, extracting the genome, and reassembling particles with the viral proteins (e.g., influenza virus polypeptide) and lipids to form lipid particles containing viral proteins.

In certain embodiments, provided herein are subunit vaccines comprising a viral polypeptide in combination with a saponin and an agonist of the intracellular stimulator of interferon genes pathway. In certain embodiments, the subunit vaccine is prepared using influenza virus that is propagated in embryonated chicken eggs.

In certain embodiments, provided herein are immunogenic compositions/vaccines comprising an inactivated virus containing a viral peptide (e.g., a chimeric influenza virus hemagglutinin polypeptide and/or an influenza virus neuraminidase polypeptide) in combination with a saponin and an agonist of the intracellular stimulator of interferon genes pathway.

Compositions described herein may be delivered to a subject by a variety of routes. These include, but are not limited to, intranasal, intratracheal, oral, intradermal, intramuscular, intraperitoneal, transdermal, intravenous, conjunctival, and subcutaneous routes. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, a composition is not formulated for administration by injection.

In certain embodiments, immunogenic compositions disclosed herein are administered intradermally. In certain embodiments, this disclosure contemplates administration using a transdermal patch for diffusion of the drug across the skin or by microneedle injection. In certain embodiments, it may be desirable to introduce the pharmaceutical compositions into the lungs by any suitable route. Pulmonary administration can also be employed, e.g., by use of an inhaler or nebulizer, and formulation with an aerosolizing agent for use as a spray.

In some embodiments, cells stimulated with vaccine and adjuvant combinations disclosed herein in vitro may be introduced (or re-introduced) into a subject using techniques known to one of skill in the art. In some embodiments, the cells can be introduced into the dermis, under the dermis, or into the peripheral blood stream. In some embodiments, the cells introduced into a subject are preferably cells derived from that subject, to avoid an adverse immune response. In other embodiments, cells also can be used that are derived from a donor host having a similar immune background. Other cells also can be used, including those designed to avoid an adverse immunogenic response.

In certain embodiments, provided herein are devices with a needle or an array of needles for intradermal administration wherein the needle(s) and used to administer compositions disclosed herein and/or the needles are coated with vaccine compositions and adjuvant mixtures disclosed herein. In certain embodiments, the vaccines comprise an inactivated virus, attenuated virus, virus protein, virus like particle, or virosome in combination with a saponin and an agonist of the intracellular stimulator of interferon genes pathway. In certain embodiments, the needles may be hollow or solid and made out of a biodegradable material.

In certain embodiments, provided herein is a device comprising a substrate having an array of microneedles for intradermal administration wherein the needles are coated with a vaccine and an adjuvant composition comprising a saponin and an agonist of the intracellular stimulator of interferon genes pathway. In certain embodiments, the microneedle devices include a substrate; one or more microneedles; and, optionally, a reservoir for delivery of drugs, as well as pump(s), sensor(s), and/or microprocessor(s) to control the interaction of the foregoing. In certain embodiments, the microneedles are between 1 µm and 1 mm long, inclusive or are between 10 µm and 500 µm long, inclusive or are between 30 µm and 200 µm long, inclusive. In certain embodiments, the microneedles have a cross-sectional dimension between 10 nm and 1 mm, inclusive or have a cross-sectional dimension between 1 µm and 200 µm, inclusive, or have a cross-sectional dimension between 10 µm and 100 µm, inclusive, or have a circular cross section with an outer diameter between 10 µm and 100 µm, inclusive. The substrate includes the base to which the microneedles are attached or integrally formed. A reservoir may also be attached to the substrate.

In certain embodiments, microneedles of the substrate can be constructed from a variety of materials, including metals, ceramics, semiconductors, organics, polymers, biodegradable polymers, and composites. Preferred materials of construction include pharmaceutical grade stainless steel, gold, titanium, nickel, iron, gold, tin, chromium, copper, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluoroacetate (TEFLON™), and polyesters.

Although viral vaccines with specified adjuvants are exemplified used herein, it is contemplated the one can apply methods and use compositions disclosed herein for vaccination against other infectious microbes such as bacteria, fungus, or other parasites.

Agonists of the Intracellular Stimulator of Interferon Genes (STING) Pathway

Stimulator of interferon genes (STING) is a protein that in humans is encoded by the TMEM173 gene. STING induces type I interferon production when cells are infected with intracellular pathogens. Cyclic di-nucleotides are agonists of the intracellular stimulator of interferon genes (STING) pathway. The signaling cascade triggered by activation of STING leads to production of IFN and other cytokines important for innate immunity. However, rather high amounts of cGAMP or other cyclic di-nucleotides have been required for adjuvant activity. Experiments were performed to determine whether combinations with other adjuvants increase adjuvant efficiency of the cGAMP in elderly subjects. In the presence of a membrane-active saponin-based adjuvant, the immunogenicity of an influenza subunit vaccine was assessed.

In certain embodiments, this disclosure relates to vaccination methods comprising intradermally administering to a human subject an effective amount of a virus, attenuated virus, virus protein, virus like particle, or virosome in combination with a saponin and a cyclic dinucleotide or derivative.

In certain embodiments, the cyclic dinucleotide or derivative of this disclosure is cyclic-di-AMP, cyclic-di-GMP, cyclic-di-IMP, cyclic-AMP-GMP, cyclic-AMP-IMP, cyclic-GMP-IMP, and cyclic-GMP-AMP (cGAMP). In certain embodiments, the cyclic dinucleotide or derivative of this disclosure has a fluoro substitution of one or both 2'-hydroxyls on cyclic-di-AMP, cyclic-di-GMP, cyclic-di-IMP, cyclic-AMP-GMP, cyclic-AMP-IMP, cyclic-GMP-IMP, In certain embodiments, the cyclic dinucleotide or derivative of this disclosure comprises bis-3',5' linkage between the two nucleotides or comprise one 2',5' linkage and one 3',5' linkage.

In certain embodiments, the cyclic dinucleotide or derivative of this disclosure dinucleotide is a compound of Formula I or Formula II:

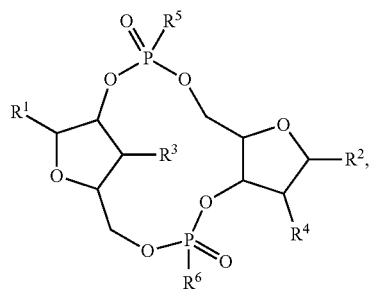

Formula I

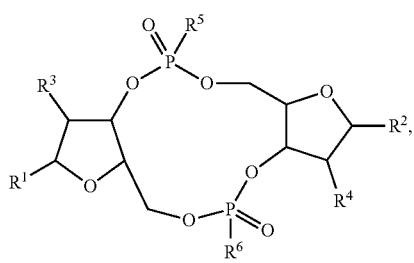

Formula II or salt thereof, wherein each $R^1$ and $R^2$ is independently a purine; each $R^3$ and $R^4$ is independently H, OH or F, and each $R^5$ and $R^6$ is independently OH or SH.

In certain embodiments, purines $R^1$ and $R^2$ are independently selected from the following structures:

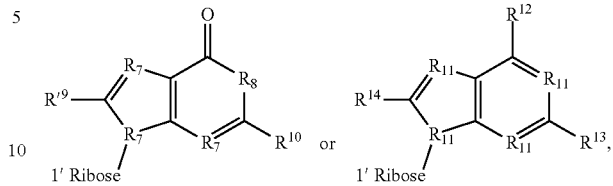

each $R_7$ or $R_{11}$ is independently —CR— or —N—;
$R_8$ is —C(R)$_2$—, —O—, or —NR—;
each $R^9$, $R^{10}$, $R^{12}$, $R^{13}$, or $R^{14}$ is independently selected from the group consisting of hydrogen, halogen, —CN, —OR, —SR, —N(R)$_2$, —C(O)R, —CO$_2$R, —S(O)R, —S(O)$_2$R, —C(O)N(R)$_2$, —SO$_2$N(R)$_2$, —OC(O)R, —N(R)C(O)R, —N(R)N(R)$_2$, —C=NOR, —N(R)C(O)N(R)$_2$, —N(R)SO$_2$N(R)$_2$, —N(R)SO$_2$R, —OC(O)N(R)$_2$ or an optionally substituted substituent selected from the group consisting of $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, and a 5-6 membered heteroaryl ring having 1-3 heteroatoms independently selected from nitrogen, oxygen, or sulfur;

wherein each R is independently an optionally substituted substituent selected from the group consisting of $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, and a 5-6 membered heteroaryl ring having 1-3 heteroatoms independently selected from nitrogen, oxygen, or sulfur, or two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur;

wherein each $C_{1-12}$ aliphatic, phenyl, 3-7 membered saturated or partially unsaturated monocyclic carbocyclic ring, 7-10 membered saturated or partially unsaturated bicyclic carbocyclic ring, 3-7 membered saturated or partially unsaturated heterocyclic ring, 7-10 membered saturated or partially unsaturated bicyclic heterocyclic ring, and 5-6 membered heteroaryl ring, or two R groups on the same nitrogen taken together to form 3-7 membered saturated, partially unsaturated, or heteroaryl ring is optionally substituted with 1 to 5, 1 to 4, 1 to 3, 1 to 2, or 1 independently selected substituents selected from the group consisting of halogen, —CN, —NO$_2$, —OH, =O, —NH$_2$, $C_{1-6}$ alkyl, $C_{1-6}$ alkoxy, $C_{1-6}$ alkylamino, and $C_{1-6}$ di-alkylamino.

In certain embodiments, purines $R^1$ and $R^2$ are independently selected from adenine, guanine, isoguanine, hypoxanthine, or xanthine.

In certain embodiments, the cyclic dinucleotide is 2',3'-cGAMP (cyclic [G(2',5')pA(3',5')p]):

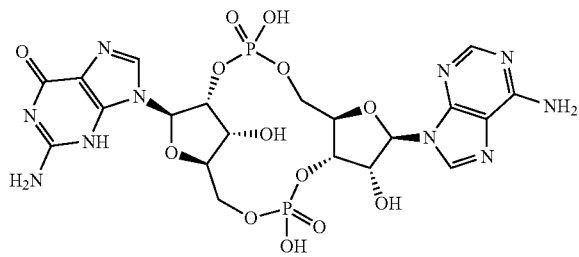 [SMILES: Nc1nc(=O)c2ncn([C@@H]3O[C@@H]4COP(=O)(O)O[C@H]5[C@@H](O)[C@H](n6cnc7c(N)ncnc76)O[C@@H]5COP(=O)(O)O[C@@H]3[C@@H]4O)c2[nH]1]

derivative, ester, or salt thereof.

Adjuvant Saponins Purified from an Aqueous Extract of the Bark of the South American Tree, *Quillaia saponaria* Molina "Quil-A," refers to an adjuvant mixture of triterpenoid quillaic acids glycosidically linked to carbohydrate moieties isolated from the bark of the South American tree, *Quillaja saponaria* Molina. See U.S. Pat. No. 5,057,540. Quil-A veterinary applications induces humoral and cellular responses. However, Quil-A is typically considered unsuitable for human use due to its highly complex mixture nature. "QS-21" is a purified component of Quil-A useful as an adjuvant. See U.S. Pat. No. 6,231,859. For example, ASO1 adjuvant contains QS-21 and 3-O-desacyl-4'-monophosphoryl lipid A (MPL). Malaria vaccine studies with using ASO1 adjuvant showed enhanced immunogenicity in intramuscular-based vaccinations. See The RTS,S Clinical Trials Partnership reports results of a phase 3 trial of RTS,S/AS01 malaria vaccine in African children. N Engl J Med, 2011, 365, 1863-1875.

Saponins may be purified from an aqueous extract of the bark of the South American tree, *Quillaja saponaria* Molina. The predominant purified *Quillaja saponins* have been identified as fractions QA-7, QA-17, QA-18, and QA-21. These saponins may be purified by high pressure liquid chromatography (HPLC) and low-pressure silica chromatography. In certain embodiments, QA-19 may be removed from the other components.

Aqueous extracts of the *Quillaja saponaria* Molina bark may be dialyzed against water. The dialyzed extract may be lyophilized to dryness, extracted with methanol, and the methanol-soluble extract may be further fractionated on silica gel chromatography and by reverse phase high pressure liquid chromatography (RP-HPLC) as described in U.S. Pat. No. 5,057,540. Peaks (denominated QA-1 to QA-22) are reported to be separable. Each peak exhibited a single band on reverse phase thin layer chromatography. The individual components were identified by retention time on a Vydac C4 HPLC column as reported in U.S. Pat. No. 5,057,540.

The substantially pure QA-7 saponin is characterized as having immune adjuvant activity, containing about 35% carbohydrate per dry weight, having a uv absorption maxima of 205-210 nm, a retention time of approximately 9-10 minutes on RP-HPLC on a Vydac C4 column having 5 µm particle size, 330 Å pore, 4.6 mm ID×25 cm L in a solvent of 40 mM acetic acid in methanol/water (58/42; v/v) at a flow rate of 1 ml/min, eluting with 52-53% methanol from a Vydac C4 column having 5 µm particle size, 330 Å pore, 10 mM ID×25 cm L in a solvent of 40 mM acetic acid with gradient elution from 50 to 80% methanol, having a critical micellar concentration of approximately 0.06% in water and 0.07% in phosphate buffered saline, causing no detectable hemolysis of sheep red blood cells at concentrations of 200 µg/ml or less, and containing the monosaccharide residues terminal rhamnose, terminal xylose, terminal glucose, terminal galactose, 3-xylose, 3,4-rhamnose, 2,3-fucose, and 2,3-glucuronic acid, and apiose.

The substantially pure QA-17 saponin is characterized as having adjuvant activity, containing about 29% carbohydrate per dry weight, having a UV absorption maxima of 205-210 nm, a retention time of approximately 35 minutes on RP-HPLC on a Vydac C4 column having 5 µm particle size, 330 Å pore, 4.6 mm ID×25 cm L in a solvent of 40 mM acetic acid in methanol-water (58/42; v/v) at a flow rate of 1 ml/min, eluting with 63-64% methanol from a Vydac C4 column having 5 µm particle size, 330 Å pore, 10 mm ID×25 cm L in a solvent of 40 mM acetic acid with gradient elution from 50 to 80% methanol, having a critical micellar concentration of 0.06% (w/v) in water and 0.03% (w/v) in phosphate buffered saline, causing hemolysis of sheep red blood cells at 25 µg/ml or greater, and containing the monosaccharide residues terminal rhamnose, terminal xylose, 2-fucose, 3-xylose, 3,4-rhamnose, 2,3-glucuronic acid, terminal glucose, 2-arabinose, terminal galactose and apiose.

The substantially pure QA-18 saponin is characterized as having immune adjuvant activity, containing about 25-26% carbohydrate per dry weight, having a UV absorption maxima of 205-210 nm, a retention time of approximately 38 minutes on RP-HPLC on a Vydac C4 column having 5 µm particle size, 330 Å pore, 4.6 mm ID×25 cm L in a solvent of 40 mM acetic acid in methanol/water (58/42; v/v) at a flow rate of 1 ml/min, eluting with 64-65% methanol from a Vydac C4 column having 5 µm particle size, 330 Å pore, 10 mm ID×25 cm L in a solvent of 40 mM acetic acid with gradient elution from 50 to 80% methanol, having a critical micellar concentration of 0.04% (w/v) in water and 0.02% (w/v) in phosphate buffered saline, causing hemolysis of sheep red blood cells at concentrations of 25 µg/ml or greater, and containing the monosaccharides terminal rhamnose, terminal arabinose, terminal apiose, terminal xylose, terminal glucose, terminal galactose, 2-fucose, 3-xylose, 3,4-rhamnose, and 2,3-glucuronic acid.

The substantially pure QA-21 saponin is characterized as having immune adjuvant activity, containing about 22% carbohydrate per dry weight, having a UV absorption maxima of 205-210 nm, a retention time of approximately 51 minutes on RP-HPLC on a Vydac C4 column having 5 µm particle size, 330 Å pore, 4.6 mm ID×25 cm L in a solvent of 40 mM acetic acid in methanol/water (58/42; v/v) at a flow rate of 1 ml/min, eluting with 69 to 70% methanol from a Vydac C4 column having 5 µm particle size, 330 Å pore, 10 mm×ID 25 cm L in a solvent of 40 mM acetic acid with gradient elution from 50 to 80% methanol, with a critical micellar concentration of about 0.03% (w/v) in water and 0.02% (w/v) in phosphate buffered saline, causing hemolysis of sheep red blood cells at concentrations of 25 µg/ml or greater, and containing the monosaccharides terminal rhamnose, terminal arabinose, terminal apiose, terminal xylose, 4-rhamnose, terminal glucose, terminal galactose, 2-fucose, 3-xylose, 3,4-rhamnose, and 2,3-glucuronic acid.

EXAMPLES

Methods

Female BALB/c (AnNCrl) mice from Charles River Labs (Wilmington, MA) were used in all experiments. Mice were housed and subjected to a 12/12-h light/dark cycle until they reached 4 (adults) or 19 (aged) months of age. H1N1 Influenza A/California07/09 virus was obtained from the Centers for Disease Control and Prevention (CDC, Atlanta, GA), grown in MDCK cells and used for hemagglutination inhibition (HAI) titration of sera. The virus was mouse-adapted by serial passage in the lungs of adult BALB/c mice and was used in challenge experiments. Influenza A (H1N1) 2009 A/California/07/09 H1N1 vaccine was obtained from BEI resources (NR-20347).

The AddaVax™ formulation is an oil-in-water emulsion with about 160 nm in diameter (e.g., 140-170 nm or 130-180 nm in diameter). The stock solutions of Quil-A and cGAMP (2',3'-cyclicGAMP) were prepared in 50 mM potassium phosphate buffer, pH 7.4. AddaVax™ (nanoemulsions produced from Span™ 85 (sorbitan trioleate 0.5%) in 5% squalene oil and 0.5% Tween™ 80 (Polyoxyethylene (80) sorbitan monooleate, 0.5%) in 10 mM sodium citrate buffer pH 6.5), 25 μl per dose, was mixed with the same volume of vaccine prior to immunization. Except for the high dose vaccine formulation, the amount of vaccine antigen was 1 μg in animal experiments. The immunogen was mixed with Quil-A in a vaccine/adjuvant ratio between 1:1 and 1:10 and with cGAMP between 1:1 and 1:5 (wt/wt, μg), as specified for each experiment.

BALB/c mice were employed that were 19 months old at the time of vaccination and are classified as aged, as well as 4-month-old mature adult mice. Mice were immunized once intramuscularly (IM) by injection (0.05 ml volume, 30-gauge needle) either into the upper quadrant of the hind leg, or intradermally (ID) into depilated dorsal skin (bleb was observed) under xylazine/ketamine anesthesia. Blood samples were collected from the fascial vein on days 7, 14, and 28 post vaccination and analyzed for HAI titers and vaccine-specific immunoglobulins. HAI titers were converted into log 2 values for statistical analysis. For challenge studies, aged mice were infected with approximately 300 plaque forming units (pfu) of the mouse-adapted virus, and adult mice received a 10-fold higher dose which was equivalent to 70×LD$_{50}$. Challenge was performed by intranasal installation of 30 μl of diluted virus under brief isofluorane anesthesia 5.5 weeks after single immunization. Mice were monitored for signs of infection for 2 weeks. The humane endpoint used for euthanasia was 25% loss of the initial body weight.

HeLa cells and murine embryonic fibroblasts isolated from the wild type (STING+/+) or STING knockout (STING−/−) mice with C57BL/6J genetic background, were grown in 48-well plates in DMEM media supplemented with 1% FBS and Penn/Strep antibiotics. Confluent cells were treated with A/California/07/09 H1N1 vaccine and individual adjuvants or their combination for 1 h at 37° C., after which they were immediately collected on ice into reducing Laemmli sample buffer supplemented with protease inhibitors, phosphatase inhibitors and DNAse I. Cell lysates were analyzed by SDS-PAGE and western blot, and probed for pIRF3 and actin using antibodies and ECL detection and imager software for quantification.

cGAMP and Quil-A as Individual Adjuvants in Aged Mice

The effects of cGAMP or Quil-A administered were explored with 1 μg of purified hemagglutinin (HA) of A/California 07/09 (H1N1) virus as a vaccine to evaluate candidate adjuvants in aged mice. The unadjuvanted vaccine was not protective: only 22% of vaccinated animals survived the challenge. In experiments all aged mice immunized intradermally (ID) with the vaccine supplemented with 5 μg cGAMP succumbed to infection upon challenge (FIGS. 1A,B). Quil-A alone, in a 5 μg dose, increased survival from 22 to 75% (FIG. 1A) with about 14% maximal weight loss (FIG. 1B). Compared with the unadjuvanted vaccine, the Quil-A supplemented formulation induced a significant 10 to 30-fold increase in vaccine-specific antibody levels, while cGAMP alone induced 3 to 4-fold increase in IgG1 and IgG/IgM by day 14 (FIGS. 1C-F). The use of Quil-A as adjuvant elicited an increase in the IgG2a level by seven fold detected as soon as day 7 of vaccination (FIG. 1E), but the changes in the IgG2a/IgG1 ratios were not statistically significant between groups of vaccinated mice (FIG. 1G), and the HAI titers remained mostly below the level of detection in all groups (FIG. 1H). These data indicate that in aged mice, Quil-A alone is more effective than cGAMP alone at the concentrations tested, but neither adjuvant ensured complete protection against live virus challenge.

Effect of Quil-A+cGAMP Combination in Aged Mice

Aged mice were immunized with the same vaccine adjuvanted with a combination of 5 μg of each compound by ID or IM injections. It was observed that survival of the ID-immunized animals increased from 22 to 80%, with a 12% average weight loss after challenge. When this formulation was delivered IM, a remarkable improvement was observed in survival from zero to 100%, and the average maximal weight loss was as low as 5% in this group (FIGS. 2A,B). All isotypes of vaccine-induced antibodies increased to a greater extent than was observed with the individual adjuvants (compare in FIGS. 1C-E and 2C-E). In particular, the levels of IgG2a isotype antibodies exhibited a 10-15-fold increase on day 7 post vaccination in the IM or ID groups, respectively, compared to the unadjuvanted vaccine delivered by the same route (insert on FIG. 2E). The difference reached 93-fold in the ID group 1 week later. By day 28 the level of vaccine specific IgG2a rose slightly in the unadjuvanted groups, but it remained significantly higher in the adjuvanted groups (FIG. 2E). A significant 10-fold increase in the vaccine-specific IgG2a/IgG1 ratio, indicative of a Th-1 shift in the immune response, was observed in the adjuvanted vs. non-adjuvanted ID group at day 7 of vaccination (p=0.003, Student two-tailed t-test) and an about 3-fold increase (p=0.051, Student two-tailed t-test) was detected between the corresponding IM groups (FIG. 2G).

Almost all aged mice in the Quil-A/cGAMP combination groups developed HAI titers of 10 or 20 by day 28 (FIG. 2H). This substantial improvement in protection and functional antibody titers over non-adjuvanted vaccine exceeded the effects of the individual adjuvants, demonstrating a synergy between them.

Comparison of Quil-A/cGAMP Combinations in Mature Adult vs. Aged Mice

Groups of mature adult mice were challenged ID or IM for vaccination with a 10-fold higher infectious dose compared to the aged animals. The groups were ranked by rate of survival and average weight loss (FIG. 3). In spite of the high infectious dose, even those adult mice that received an unadjuvanted vaccine were partially protected, with 60 and 80% survival rates observed in the ID and IM groups, respectively, and all adjuvants in the doses tested except for 1 μg cGAMP completely prevented mortality. Differences in protection in the Quil-A/cGAMP combination group (5 μg each) delivered ID or IM were not observe (FIG. 3). In the adult mice, the maximal geometric mean HAI titer 45.9 was detected in the 5 μg Quil-A group, while in the aged mice this was detected in the Quil-A/cGAMP combination groups using 5 μg of each (FIG. 2H). Quil-A alone (5 μg) increased vaccine-specific antibody levels as effectively as in combination with 1-5 μg cGAMP. A drop in the level of vaccine-specific IgM from day 7 to day 28 in mature adults (FIG. 4A) was accompanied by a corresponding increase of vaccine-specific IgG (FIG. 4C). The initial IgM response was 3-4 fold lower in the aged animals than in the adults (compare FIGS. 4A,B) and a 1.6-fold increase of vaccine-specific IgM in the Quil-A/cGAMP group was observed between days 7 and 14 (p=0.04), but essentially remained at day 7 levels in the Quil-A group (FIG. 4B). An increase in the level of vaccine-specific IgG was observed between days 7 and 14 in the aged animals (FIG. 4D), but it was about 20-fold lower than observed in the adult mice by day 28 (FIG. 4C). These data indicate that the adjuvant combination improved antibody class switching in the aged mice, but this process was significantly more efficient in the adult animals without use of an adjuvant.

Mechanism of Potentiation of cGAMP Signaling by Quil-A

Binding of cGAMP to the STING adaptor protein triggers phosphorylation of the downstream factor IRF3. We compared the effect of each adjuvant alone or in combination on IRF3 phosphorylation in HeLa cells, which are known to respond to cGAMP. The cells were incubated with adjuvants for 1 hour, followed by assay of phosphorylated IRF3 levels in cell lysates by western blot (FIG. 5A). Comparison of the intensities of the pIRF3 band normalized to actin showed that the addition of vaccine or Quil-A did not change pIRF3 levels, while cGAMP increased them up to 3-fold in a concentration-dependent manner (FIG. 5B). A combination of Quil-A and cGAMP yielded the highest increase, about 8-fold, in pIRF3 levels as compared to untreated control. Notably, in the presence of 5 µg/ml cGAMP the increase in concentration of Quil-A from 5 to 10 µg/ml increased phosphorylation of IRF3 in HeLa cells six-fold (FIG. 5B). Same experiments carried out in MEFs provided similar results and confirmed that phosphorylation of IRF3 was due to STING activation because it only occurred in STING+/+ but not in STING−/− MEFs. These results support the conclusion that Quil-A enhances access of cGAMP to STING, and demonstrate that the combination of these compounds activates the IRF3 complex more effectively than cGAMP alone.

Comparison with Current Approaches for Vaccination in Aged Humans

Experiments were performed to determine whether a cGAMP/QuilA combination was more effective than the two currently used approaches for boosting the human immune response in aged patients. Aged mice were administered a single dose of 1 µg vaccine alone or in combination with a squalene-based adjuvant, AddaVax™, which, according to the manufacturer instruction, is similar to the MF59 formulation used in humans. Addition of AddaVax™ increased survival after lethal challenge to 60% in both IM and ID groups (FIG. 6A), but did not prevent high ~19% average weight loss at day 7 post challenge (FIG. 6B). Consistent with previously reported data for a similar squalene-based adjuvant, the levels of vaccine-specific immunoglobulins were significantly elevated in the AddaVax™ groups as compared to the vaccine only groups (FIGS. 6C-E). The vaccine-specific IgG/IgM ratio in the AddaVax™ groups was also consistently higher than in non-adjuvanted groups (FIG. 6F), indicating an increase in the efficiency of antibody class switch. Changes were not observed in the vaccine-specific IgG2a/IgG1 ratio (FIG. 6G) indicating a change in the Th type of response. Although aged animals immunized IM with the adjuvanted formulation demonstrated slightly higher levels of vaccine-specific IgG and IgG1 and IgG/IgM ratio as compared to the ID-vaccinated mice, survival percentages were similar for both delivery routes. The aged mice developed very low HAI titers which were at or below the limit of detection in all groups in response to a single 1 µg vaccination dose (FIG. 6H). In comparison, AddaVax' effectively prevented mortality in vaccinated mature adult mice (4-month-old control). Thus, although very effective in adults, AddaVax' did not effectively prevent mortality or lessen morbidity in aged animals.

Experiments were performed to determine whether an ID vaccination with a 4-fold higher dose of an unadjuvanted antigen was protective in the aged mice. A significant amount (75%) of mice in the 4 µg dose group survived the challenge, compared to 22% survival in the 1 µg vaccine group (FIG. 7A), but the maximal weight loss was as high as 16% (FIG. 7B). No significant differences were observed in the levels of vaccine-specific IgG, IgG1, IgG2a, or in IgG/IgM and IgG2a/IgG1 ratios (FIGS. 7C-G) that would correlate with better survival in the 4×antigen dose group, and HAI titers were mostly below the level of detection in both groups (FIG. 7H). Thus, in aged mice, use of a 4-fold higher antigen dose yielded a comparable level of protection as that observed with the AddaVax' adjuvant. In both cases, survival was improved, although not to 100%, but morbidity was not prevented as seen by significant weight loss observed in all groups after challenge. These data show that the current strategies used to vaccinate the aged population are also limited in their effectiveness in the aged mouse model. In particular, the improvement in protection and functional antibody titers over non-adjuvanted vaccine was reduced compared with the cGAMP/Quil-A combination, demonstrating the high potential of this adjuvant combination in overcoming the effects of immunosenescence.

What is claimed is:

1. An influenza vaccination method comprising administering intramuscularly and/or intradermally to a human subject more than 65 years old an effective amount of an influenza vaccine in combination with a mixture of purified *Quillaja saponins* QA-7, QA-17, QA-18, and QA-21, wherein the mixture of saponins is formulated with squalene nanoparticles comprising sorbitan trioleate and polyoxyethylene sorbitan monooleate, and a cyclic dinucleotide, wherein the cyclic dinucleotide is 2',3'-cGAMP.

* * * * *